United States Patent [19]

Varela

[11] Patent Number: 4,584,522
[45] Date of Patent: Apr. 22, 1986

[54] DIGITAL DIRECT READING GRAIN MOISTURE TESTER

[75] Inventor: Marco E. Varela, Boardman, Ohio

[73] Assignee: Electrex, Inc., Aurora, Ohio

[21] Appl. No.: 522,027

[22] Filed: Aug. 11, 1983

[51] Int. Cl.⁴ ............................................. G01R 27/26
[52] U.S. Cl. ............................. 324/61 R; 324/60 CD; 73/336.5
[58] Field of Search ................. 324/61 R, 60 R, 60 C, 324/60 CD, 61 P, 65 R; 73/73, 74, 335, 336.5; 340/602

[56] References Cited

U.S. PATENT DOCUMENTS

| 3,427,537 | 2/1969 | Osborne | 324/65 R |
| 3,648,165 | 3/1972 | Shawhan | 324/60 R |
| 4,399,404 | 8/1983 | Resh | 324/61 R |

OTHER PUBLICATIONS

Electrex Inc., Grain Moisture Testing, 20 page Operating Manual.
Single-Chip 3½-Digit Low-Power A/D Converter, IC Master 1982, Intersil Inc., pp. 2207-2214.
Electronic Portable Moisture Tester, Electrix Inc., 2 page Promotional Flyer.

Primary Examiner—Reinhard J. Eisenzopf
Assistant Examiner—Jack B. Harvey
Attorney, Agent, or Firm—Body, Vickers & Daniels

[57] ABSTRACT

A direct measuring digital grain moisture meter comprises a light weight power supply, an oscillator, a two plate capacitor having a receptacle admitting a grain sample acting as the capacitor dielectric, and a detector/display measuring the dielectric constant and hence moisture content of the grain sample and displaying a numeric representation the moisture content of the grain. The meter provides a direct reading of grain moisture content requiring no further mathematical manipulation by the user or external temperature compensation.

10 Claims, 2 Drawing Figures

DIGITAL DIRECT READING GRAIN MOISTURE TESTER

BACKGROUND OF THE INVENTION

The present invention relates to the art of measuring the moisture content of grains or like materials. More particularly, the present invention provides a direct reading moisture meter visually indicating the moisture content of a grain sample.

The moisture content of grains and like material has a direct consequence on the market value of grain, the ability to store the grain for prolonged periods, and the usability of the grain in processing and manufacturing apparatus. The moisture content in grain must, therefore, be monitored by the farmer, the elevator man, and the processor.

The most readily apparent indication of the importance of grain moisture content is the differential in price paid for grains of different moisture content. Grains with too high of a moisture content sell for a lower price than grains with a correct moisture content. Moreover, grains with lower moisture content than ideal lose weight with loss of moisture and, therefore, sell for a smaller amount than grains with an ideal moisture content.

Farmers dry grain to the preferred moisture content. Done properly, this maintains the grains food value, facilitate proper storage, and increase its value. Drying operations are energy intensive and, therefore, expensive. It is therefore advantageous to monitor the moisture content of the grain during drying and avoid over drying. This is best done with a portable moisture meter which allows testing to be done at the site of drying.

Portable grain moisture meters have been available in the past. One such device was described in U.S. Pat. No. 3,427,537. This device uses a resistance bridge network which compares the resistance of a grain sample of fixed volume placed between two electrodes to the resistance of a potentiometer. The user of the tester operated a dial mechanically connected to the potentiometer and watched for a null in a indicator light. The null indicated matched resistance between the sample and the adjusted potentiometer. At a null, the calibrated dial face of the potentiometer dial indicated the moisture content of the grain. This system requires the careful balancing of a resistance bridge network to obtain a correct reading. This is difficult because of the large voltage (80 volts) needed to operate the neon bulb null indicator. Moreover, the system requires the use of calibrated dial faces and complicated circuitry and a vibrator and transformer was used to produce the 600 volts of pulsed DC power required to operate the tester. These elements consume large amounts of current, requiring a large battery. The use of a mechanical vibrator, a transformer, and a heavy battery make for a very heavy unit.

Additional problems were also present in this device. The heart of the measuring apparatus was a resistance comparing bridge. Hard knocks and the like, often encountered on a farm could effect the precision and calibration of the bridge. Additionally, the front panel required a precision calibrated dial and lamp for nulling the bridge. These delicate components can easily be damaged or knocked out of calibration.

A later designed prior art device was essentially similar to the previously described device except that the mechanical vibrator was replaced with an electronic oscillator and the nulling lamp was replaced with an ammeter. This was a significant improvement as it removed a mechanical device subject to wear and malfunction and replaced it with a much longer lived electronic circuit. However, the need of a heavy transformer and battery remained. The use of an ammeter greatly improved the accuracy of the device by allowing a more precise nulling procedure. The use of a calibrated dial face with its attendant problems continued An additional difficulty with both of the above devices was the requirement for the user to carefully monitor the temperature of the sample under test and apply a temperature compensation factor to arrive at a final value of moisture content.

The present invention contemplates a new and improved direct measuring grain moisture tester, which is much more reliable, rugged, lighter in weight, and requires less complicated activities of the operator than prior devices, thus overcoming all of the above referred to difficulties and others.

SUMMARY OF THE INVENTION

In accordance with the present invention, there is provided a digital, direct measuring grain moisture tester which measures the moisture content of grain by measuring the grain's permittivity or dielectric constant. A sample of grain of known volume is placed between the electrode plates of a capacitor and the change in the capacitance of the capacitor caused by the substitution of the grain as dielectric is measured. The change in capacitance is measured by applying an oscillator output current to the capacitor plates and measuring the effect the capacitor has on the oscillator output.

Further in accordance with the invention, circuitry is provided which inserts an offset value into the output and providing a visually perceptable representation of said output plus offset.

Still further accordance with the invention, there is provided electronic grain moisture tester having adjustable gain means and adjustable offset means allowing the use of a single test circuit for the evaluation of moisture content of various grains and other materials.

Yet further in accordance with the invention, a temperature sensing thermistor is provided in the offset circuitry automatically compensating the output of the tester for the temperature of the grain sample.

OBJECTS OF THE INVENTION

The principal object of the present invention is the provision of a digital electronic grain moisture tester which is easy to use and has a low power requirement.

Another object of the present invention is the provision of a grain moisture tester having internal temperature compensation.

Another object of the present invention is the provision of a direct measuring grain moisture tester providing a direct reading of grain moisture requiring no further mathematical manipulation by the user to arrive at a final value.

Still another object of the present invention is the provision of a grain moisture tester which is light in weight, rugged in construction, and reliable for use in the field.

BRIEF DESCRIPTION OF THE DRAWINGS

The invention may take physical form in a number of different configurations, a preferred embodiment of which will be described in detail hereinafter and illustrated in the accompanying drawings.

DESCRIPTION OF THE PREFERRED EMBODIMENT

Figure 1:
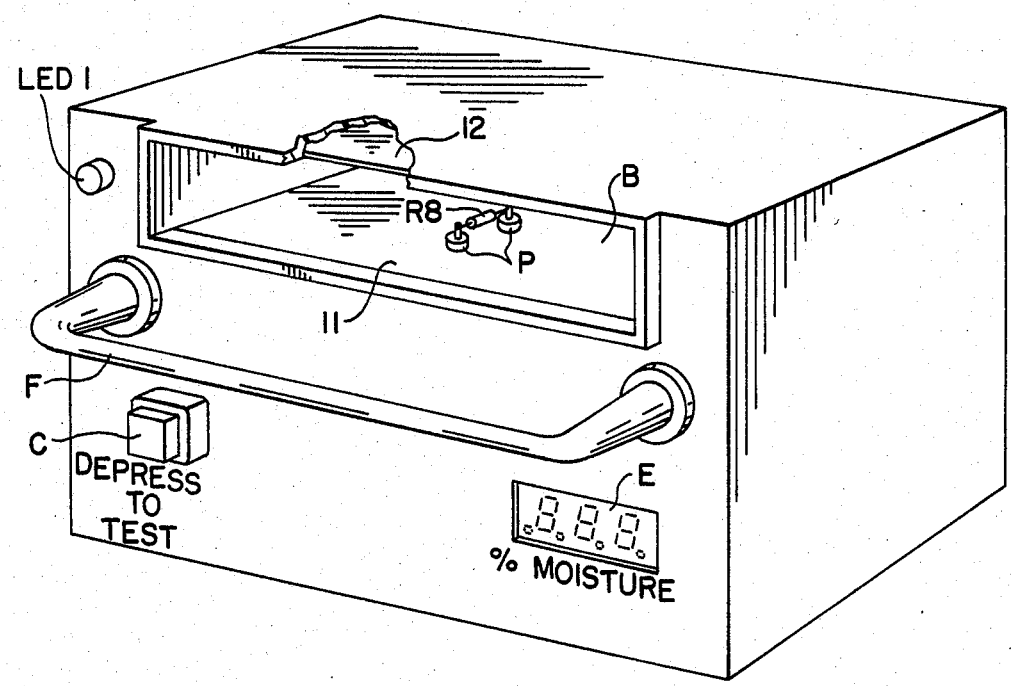
FIG. 1 is a perspective view of the finished grain moisture tester partially cut away; and, FIG. 2 is a schematic drawing of the circuit of the present invention.

Referring now to the drawings, wherein the showings are for the purpose of illustrating the preferred embodiment of the invention and not for purposes of limiting same, FIG. 1 shows the front panel of preferred embodiment of the invention. All controls necessary for operation of the device in the field are on the front panel. A sample of grain to be tested is placed in receptacle B and the entire testing unit is gently tapped on the side to settle the grain in the receptacle. Additional grain is added to fill the entire receptacle. The push button of momentary contact switch C is depressed and held depressed for 40 seconds. During this operation light emitting diode LED1 will be on indicating the unit has sufficient power to perform a test. At the end of 40 seconds, the numerical display on liquid crystal display E will have settled and will display a number having up to three digits. This number is the moisture content of the grain expressed as a percentage.

The housing of the unit is manufactured from tough plastic and provided with a carrying handle F. The device is rugged and well suited to use in the field.

Figure 2:
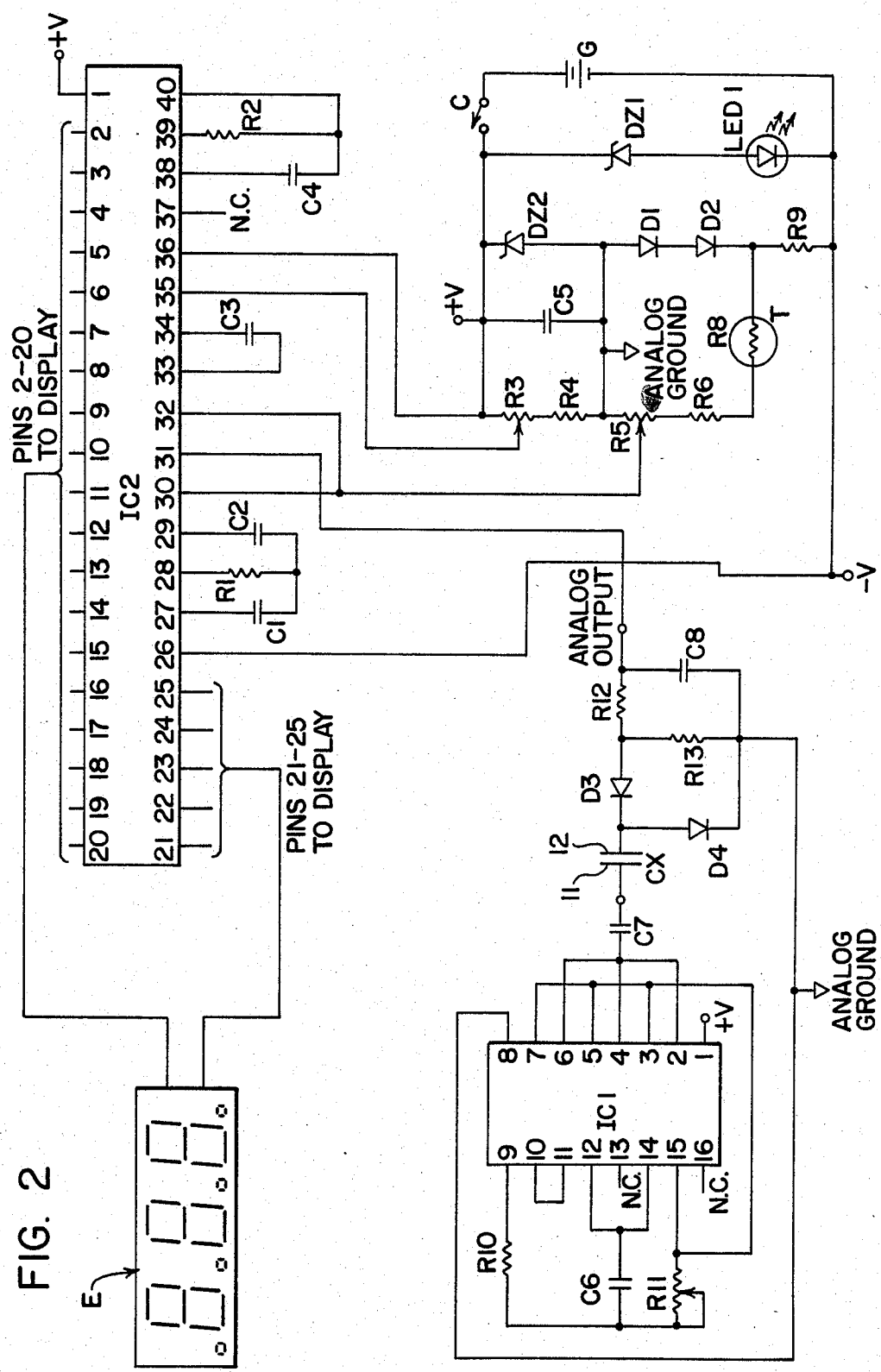

The electronic circuitry which performs the actual moisture content measurement and provides the digital display seen in liquid crystal display E, is shown in FIG. 2 The cirucuit can be broken down into three sub-circuits, an oscillator, a detector/display and a power supply.

The Oscillator

Integrated circuit IC 1 shown in FIG. 2, is a buffered hex inverter. The integrated circuit contains six buffered inverters which are interconnected in the present invention to form a square wave oscillator. A CMOS integrated circuit designated CD4049, Series B, is used. It has been found that integrated circuit CD4049CN, available from National Semiconductor Corporation of Santa Clara, California, operates best in this circuit. Three of the hex inverters are interconnected by resistors R10, Rll and capicitor C6 to form a feed back oscillator. The remaining three hex inverters are connected in parallel to the output of the feedback oscillator providing a higher power output square wave. IC 1 is powered with a regulated 5.1 volt positive input at its number 1 pin and fixed to analog ground at its number 8 pin. The output of the three hex inverters is provided at pins 2, 4, and 6, which are tied together, and is a two megahertz square wave having a 5 volt peak-to-peak amplitude.

Detector/Display

The output of IC 1 is applied through isolation capicitor C7 to electrodes 11 and 12 forming a capacitor CX of variable capacitance. Plates 11 and 12 are also seen in FIG. 1. Plates 11 and 12 are rectangular aluminum plates measuring 5¾ inches by 6 inches. The two plates are spaced one inch apart and form a capacitor which has a capacitance measured in picofarads when filled with air. In a grain moisture test, the space between the two plates is filled with a grain sample. Thus, the grain sample forms the dielectric between the two plates.

The dielectric constant of a grain is dependent upon its moisture content. The dielectric constant of the sample will determine the capacitance value of the capacitor CX formed by the two plates 11 and 12. The dielectric constant or permittivity of grain is much higher than that of air and the grain filled capacitor CX will have a value measured in the hundreds of picofarads Test capacitor CX will be alternately charged and discharged by the two megahertz square wave produced by IC1 During the charging half cycle, current will pass through CX and diode D4 to analog ground. The charging will be rapid, as the only resistance in the circuit is the inherent resistance of the wiring and the resistance of diode D4. During the discharging half cycle, CX will discharge through diode D3 and resistor R13. The rate of discharge will be determined by the time constant of the RC circuit formed by CX and R13. At the end of a discharge half cycle, the charging cycle will begin again with some charge remaining on capacitor CX. A net average positive voltage will therefore be present at the interconnection of diode D3 and resistor R13 indicative of the capacitance of CX and hence the dielectric constant of the grain sample under test.

Resistor R12 and capacitor C8 form a low-pass filter which will stabilize the voltage at the anode of diode D3 and provide an analog output voltage representative of the charge retained on capacitor CX, its capacitance value, and hence the dielectric constant of the material contained between the plates 11 and 12. This voltage is representative of the moisture content of the grain being tested.

The analog output is applied to pin 31 of integrated circuit IC2. IC2 is either an ICL7126 or an ICL7136 low power analog to digital convertor available from Intersil, Inc. of Cupertino, California. The ICL7136 has certain advantages such as extremely low power consumption when compared to the ICL7126. However, the ICL7126 is more readily available at the present time, and is, therefore, used in the preferred embodiment. Pins 2 through 25 of IC2 are connected directly to liquid crystal display E. These connections supply all information and power needed to drive the display.

Pins 38, 39 and 40 of IC2 are interconnected with capacitor C4 and resistor R2. This forms an internal oscillator in accordance with manufacturer's instructions which causes IC2 to read the analog input on Pin 31 three times per second and provide an output repre sentative of this input to liquid crystal display E Capacitors Cl, C2 and resistor R1 are selected to set the full range scale of IC2, minimize noise, and provide zeroing reference as required by the chip.

Capacitor C3 is the reference capacitor used by IC2 to hold the charge delivered by the analog input at Pin 31 during analog to digital conversion. In the present invention, capacitor C3 is selected to have a much larger value than that recommended by the manufacturer of IC2. This improves accuracy in the present invention without any adverse consequences as a steady voltage is being measured Pins 35 and 36 provide reference input and allow scaling of the output of IC2. Pin 36 is directly connected to the positive supply bus of the power supply. Pin 35 is connected to the wiper of potentiometer R3. Potentiometer R3 and resistor R4 are connected as a voltage divider between the positive supply bus and the analog ground. Adjustment of potentiometer R3 supplies a reference voltage which is adjustable to scale the output of the tester.

The dielectric constant or permittivity of a sample of grain is dependent on the temperature as well as on its moisture content. Moreover, moisture content is not directly proportional to dielectric constant. An offset compensation circuit is provided for more precise tracking of the output of the tester to actual moisture content. IC2 Pins 30 and 32 are inter-connected and connected to potentiometer R5. Potentiometer R5, resistor R6, and thermistor R8 form a voltage divider between the analog ground and a point in the power supply regulated at 1.4 volts below analog ground. The offset of the display generated by IC2 is set by adjusting potentiometer R5. This provides an offset voltage between the analog ground potential, which is the lowest potential which can be reached by the analog input, and negative 1.4 volts. The base offset is set by adjusting R5.

The base offset is automatically adjusted to compensate for the temperature of the grain by thermistor R8. Thermistor R8 is located inside receptacle B. Thermistor R8 is supported by isolation posts P well above electrode plate 11 and will be completely surrounded by the grain sample during testing. During the 40 second settling period recommended, thermistor R8 senses the temperature of the grain. The resistance of the thermistor changes in response to the temperature and adjusts the offset voltage divider composed of R5, R6 and R8 to compensate for the temperature of the grain.

The Power Supply

Power is supplied to the circuit by a nine volt alkaline battery G. The positive supply of the battery is connected through momentary contact switch C to the positive supply bus V+ of the circuit. The negative supply of the battery is directly connected to the negative supply bus V− of the circuit.

A battery test circuit is connected to switch C and always engaged when switch C is depressed. Zener diode DZ1 is rated at 5.1 volts and connected between the positive supply bus and light emitting diode LED1 which is in turn connected to the negative supply bus. LED1 requires only 2.76 volts to enter its light emitting state. Therefore, so long as battery G is capable of supplying 7.86 volts, LED1 will be illuminated indicating that the battery is supplying sufficient energy to run the circuit.

The power supply is regulated by a voltage divider comprising Zener diode DZ2, diode D1, diode D2, and resistor R9. Zener diode DZ2 is rated at 5.1 volts and is connected between the positive supply bus and the analog ground bus. This provides a regulated potential difference between the positive supply bus and analog ground of 5.1 volts. Diodes D1 and D2 are connected between the analog ground R9 and thermistor R8. These two diodes, when forward biased, provide a voltage drop of 1.4 volts as required for the offset circuit. R9 is small value resistor limiting the current through the voltage regulator divider.

Capacitor C5 is connected between the positive supply voltage bus and the analog ground. The capacitor supplies noise suppression and regulation for the power supply pins of the integrated circuits and the reference gain circuit.

Preferred component values are set forth below:

| CAPACITORS (Microfarads) | RESISTORS (Ohms) | DIODES |
|---|---|---|
| C1 0.1 | R1 1.0 meg | D1 IN4148 OR IN914 |
| C2 0.47 | R2 560k | D2 IN4148 OR IN914 |
| C3 1.0 | R3 20k pot | D3 IN914 OR IN4148 |
| C4 0.000056 | R4 30k | D4 IN914 OR IN4148 |
| C5 0.1 | R5 10k pot | DZ1 IN751 |
| C6 0.00002 | R6 470 | DZ2 IN751 |
| C7 0.1 | R9 150 | LED1 RTP280 |
| C8 0.01 | R10 1k | |
| | R11 5k pot | |
| | R12 1 meg | |
| | R13 1,500Ω | |

The invention has been described with a preferred embodiment. Obviously, modifications and alterations will occur to others upon the reading and understanding of this specification. It is my intention to include all such modifications and alterations in so far as they come within the scope of the appended claims or the equivalents thereof.

Having this described by invention, I claim:

1. Apparatus for directy measuring the moisture content of particulate material comprising a casing having a top well provided with an opening to a receptacle adapted to receive said particulate material with parallel electrode plates defining two opposite sides of said receptacle and forming a capacitor, an oscillator means having an output with a charging half cycle and a discharging half cycle, detector means determining the capacitance between said electrode plates comprising a capacitor charging path having a first given resistance and a diode forward biased in the charging half cycle and reverse biased during the discharging half cycle; a capacitor discharging path having a second given resistance different from said first given resistance and a diode forward biased in the discharging half cycle and reverse biased in the charging half cycle; and, an output voltage proportional to the charge retained on said electrode plate; and means converting said detector output to a visually pereceptable form.

2. The apparatus of claim 1 wherein said detector includes a low pass filter.

3. The apparatus of claim 1 wherein said second given resistance is higher than said first given resistance.

4. The apparatus of claim 1 wherein said coverting means comprises an analog to digital converter driving a digital display.

5. The apparatus of claim 4 wherein said analog to digital converter includes an offset adjustment circuit such that said digital display shows a number equal to an offset value plus a value proportional to said detector output.

6. The apparatus of claim 5 wherein said offset adjustment circuit includes a temperature sensistive element disposed in said receptacle whereby said offset value is dependent on the temperature of said particulate material.

7. Apparatus for directly measuring the moisture content of particulate material comprising a casing having a top wall provided with an opening to a receptacle adapted to receive said particulate material with parallel electrode plates forming a capacitor defining two opposite sides of said receptacle; an oscillator means having an output with a charging half cycle and a discharging half cycle; means applying said oscillator output to said electrode plates; detector means comprising a charging path for said capacitor having a low resistance and a diode forward biased in the charging half cycle and reverse biased in the discharging half cycle, a discharging path for said capacitor having a high resistance and a diode forward biased in the discharging half cycle and reverse biased in the charging half cycle and an output voltage proportional to the charge retained on said electrode plates; and, an analog to digital converter producing a visually perceptable digital representation dependent on said detector output voltage.

8. The apparatus of claim 7 wherein said analog to digital converter includes an offset adjustment circuit such that said digital display shows a number equal to an offset value plus a value proportional to said detector output.

9. The apparatus of claim 8 wherein said offset adjustment circuit includes a temperature sensistive element disposed in said receptacle whereby said offset value is dependent on the temperature of said particulate material.

10. A method of measuring the moisture content of particulate material comprising the following steps:

placing a sample of said particulate material in a receptacle having two opposite sides forming the plates of a capacitor, applying an oscillating current to said capacitor, providing a charging path having a first given resistance and a discharging path having a second given resistance different from said first given resistance for said capacitor, measuring the average charge retained on said capacitor over at least several oscillations of said oscillating current and providing a charge signal representative of said average charge, creating an offset signal dependent on the temperature of said particulate material, adding said charge signal to said offset signal to produce a total signal, and providing a visually perceptable representation of said total signal.

* * * * *